(12) United States Patent
Liu et al.

(10) Patent No.: US 8,722,335 B2
(45) Date of Patent: May 13, 2014

(54) METHODS AND KITS USED IN THE DETECTION OF FUNGUS

(75) Inventors: Cindy Liu, Flagstaff, AZ (US); Sergey Kachur, Monterey Park, CA (US); Lance Price, Flagstaff, AZ (US); Paul Keim, Flagstaff, AZ (US)

(73) Assignees: The Translational Genomics Research Institute, Phoenix, AZ (US); Arizona Board of Regents on Behalf of Northern Arizona University, Flagstaff, AZ (US)

( * ) Notice: Subject to any disclaimer, the term of this patent is extended or adjusted under 35 U.S.C. 154(b) by 42 days.

(21) Appl. No.: 13/014,645

(22) Filed: Jan. 26, 2011

(65) Prior Publication Data

US 2011/0263462 A1 Oct. 27, 2011

Related U.S. Application Data

(60) Provisional application No. 61/298,453, filed on Jan. 26, 2010.

(51) Int. Cl.
*C12Q 1/68* (2006.01)
*C07H 21/04* (2006.01)

(52) U.S. Cl.
USPC ......................................... 435/6.12; 536/23.1

(58) Field of Classification Search
None
See application file for complete search history.

(56) References Cited

U.S. PATENT DOCUMENTS

| 5,580,971 A * | 12/1996 | Mitsuhashi ................ 536/24.32 |
| 6,235,484 B1 * | 5/2001 | Hogan et al. ................. 435/6.13 |
| 2008/0248970 A1 * | 10/2008 | Morrison et al. ............... 506/16 |
| 2012/0053842 A9 * | 3/2012 | Gehrmann et al. ............. 702/19 |

FOREIGN PATENT DOCUMENTS

WO 2004044247 A2 5/2004

OTHER PUBLICATIONS van Burk, Jo-anne, Panfungal PCR Assay for Detection of Fungal Infection in Human Blood Specimens; Journal of Clinical Microbiology, May 1998, pp. 1169-1175.
Einsele, Hermann, Detection and Identification of Fungal Pathogens in Blood by Using Molecular Probes; Journal of Clinical Microbiology, Jun. 1997, pp. 1353-1360.
Kappe, R., Molecular probes for the detection of pathogenic fungi in the presence of human tissue; Journal of Medical Microbiology, Sep. 1998, vol. 47, No. 9, pp. 811-820.
Liu, Cindy M., FungiQuant: A broad-coverage fungal quantitative real-time PCR assay; BMC Microbiology, Biomed Central Ltd., vol. 12, No. 1, Nov. 8, 2012, p. 255.

* cited by examiner

*Primary Examiner* — Nancy T Vogel
(74) *Attorney, Agent, or Firm* — Polsinelli PC

(57) ABSTRACT

The invention encompasses methods of using quantitative PCR to detect fungal organisms in clinical and environmental samples and to generate standards that allow the quantification of fungal organisms in the samples.

45 Claims, 6 Drawing Sheets

METHODS AND KITS USED IN THE DETECTION OF FUNGUS

CROSS REFERENCE TO RELATED APPLICATION

This application claims priority under 35 U.S.C. §119(e) from the U.S. Provisional Application having Ser. No. 61/298,453, filed on 26 Jan. 2010, entitled COMPOSITIONS AND METHODS USED IN IDENTIFYING FUNGUS which is hereby incorporated by reference in its entirety.

FIELD OF THE INVENTION

Generally, the invention relates to molecular methods of detecting microorganisms. Specifically, the invention relates to methods of detecting a wide variety of fungal species and quantifying the total amount fungus in a sample.

BACKGROUND OF THE INVENTION

Invasive Fungal Infections (IFI) are an important cause of disease, especially in immuncompromised patients, including patients undergoing high dose chemotherapy, patients receiving stem cell and bone marrow transplants, preterm neonates, intensive care patients, and patients with acquired or innate immune deficiencies. Fungal, bacterial, viral, helminth, and other infections each require different courses of treatment and choosing the wrong treatment could cause unnecessary side effects and extend patient suffering. Clearly, a clinician needs a rapid, single diagnostic test to differentiate fungal infections from infections with other microorganisms.

Using current techniques, fungal infections are difficult to diagnose in clinical setting because fungi are difficult to culture, with the time of culture often extending beyond clinical utility and with culture failures (rendering no useful diagnostic information) frequent. (Preuner and Lion, *Expert Rev. Mol. Diagn.* 9, 397-401, 2009). This results in an under-diagnosis and under-treatment of fungal infections.

PCR amplification techniques have been used to detect fungal nucleic acids directly isolated from samples without the need for culture. The development of these techniques has been hindered by fungal contaminants that inhibit PCR (Borman et al, *J Antimicrob Chemother* 61 i7-i12, 2008) or by appropriate experimental controls that would allow the researcher to detect the presence of these or other contaminants (Khot and Fredricks *Expert Rev Anti Infect Ther* 7, 1201-1221, 2009).

A further challenge to the development of PCR assays for fungal infection is the development of a single, broad range PCR assay that detects a wide variety of fungi including a wide range of infective fungi strains and species, fungi not normally known to infect human beings, or even fungi that are not characterized. Such an assay must be broad enough to amplify the vast majority of known fungal species (including those that are difficult to culture,) but selective enough that contaminating human DNA or other contaminating DNA are not significantly amplified. Many attempts have been made, but none have done so using degenerate PCR primers. Additionally, such an assay must also be able to quantify the fungal load to provide additional clinical utility and the ability to create a clonal library for identification and quantification of individual fungal species.

BRIEF SUMMARY OF THE INVENTION

The present invention relates to primers and primer sets and methods of use of those primer sets to detect, identify, and quantify a wide variety of fungi. More specifically the invention incorporates primer sets that amplify a region of the 18S rRNA gene of fungi to provide a pan-fungal quantitative PCR detection and quantification assay. The fungi may be detected by a PCR reaction using an oligonucleotide that includes SEQ ID NO. 1 as a forward primer and an oligonucleotide that includes SEQ ID NO. 3 as a reverse primer. In one embodiment of the invention, a forward primer and a reverse primer are added to a first mixture comprising a nucleic acid isolated from a sample. The mixture is subjected to conditions that allow nucleic acid amplification and the presence or absence of fungi is detected on the basis of a result of the nucleic acid amplification. The forward primer and the reverse primer may either or both be less than 50 nucleotides in length. The method may further comprise the addition of an oligonucleotide probe that includes SEQ ID NO. 2 to the mixture. The oligonucleotide probe may be less than 50 nucleotides in length. The oligonucleotide probe may comprise a fluorescent label. The fluorescent label may be any fluorescent label including but not limited to: HEX, TET, 5-FAM, 6-FAM, JOE, Cy3, Cy5, ROX, TAMRA, dR110, dR6G, VIC, NED, dROX PET, Gold540, LIZ, and Texas Red. The oligonucleotide probe may also comprise a quencher. The quencher may be any quencher including TAMRA, BHQ1, BHQ2, BHQ+ or DABCYL. The forward primer may comprise a forward primer mixture that reflects the degeneracy in SEQ ID NO. 1. The forward primer mixture may comprise SEQ ID NO. 6 and SEQ ID NO. 7 in any proportion. The reverse primer may comprise a reverse primer mixture that reflects the degeneracy in SEQ ID NO. 3. The reverse primer mixture may comprise SEQ ID NO. 8, SEQ ID NO. 9, SEQ ID NO. 10, SEQ ID NO. 11, SEQ ID NO. 12, SEQ ID NO. 13, SEQ ID NO. 14, and SEQ ID NO. 15 in any proportion. The sample may be any sample derived from a subject such as an animal, including a human being. The sample may also be any sample derived from an environmental source.

The method may further comprise adding a second forward primer that includes SEQ ID NO. 4 to a second mixture comprising a nucleic acid isolated from the sample, adding a second reverse primer that includes SEQ ID NO. 5 to the second mixture, and subjecting the second mixture to conditions that allow nucleic acid amplification. The second forward primer may comprise a second forward primer mixture that reflects the degeneracy of SEQ ID NO. 4. The second forward primer mixture may comprise SEQ ID NO. 16, SEQ ID NO. 17, SEQ ID NO. 18, and SEQ ID NO. 19 in any proportion. The second reverse primer may comprise a second reverse primer mixture that reflects the degeneracy of SEQ ID NO. 5. The second reverse primer mixture may comprise SEQ ID NO. 20, SEQ ID NO. 21, SEQ ID NO. 22, SEQ ID NO. 23, SEQ ID NO. 24, SEQ ID NO. 25, SEQ ID NO. 26, and SEQ ID NO. 27 in any proportion. The second forward primer and the second reverse primer may each comprise a cloning sequence that facilitates cloning of the product into a nucleic acid vector. The cloning sequence may be any cloning sequence including a restriction endonuclease site. The method may further comprise ligating the product into the nucleic acid vector, measuring the copy number of the nucleic acid vector, deleting the nucleic acid vector so as to generate a standard set, and comparing a result of the nucleic acid amplification of the first mixture to a result of a nucleic acid amplification of a third mixture, wherein the third mixture comprises a standard from the standard set and thereby quantifying the amount of fungus in the sample.

In another embodiment of the invention, a fungal clone library from a sample may be generated by adding a forward primer that includes SEQ ID NO. 4 to the mixture, adding a reverse primer that includes SEQ ID NO. 5 to the mixture, and subjecting the mixture to nucleic acid amplification. The forward and reverse primers may each comprise a sequence that facilitates cloning into a nucleic acid vector. The method may further comprise isolating a product of the nucleic acid amplification and ligating the product into the nucleic acid vector. The nucleic acid vector may be any vector including a plasmid vector.

In another embodiment of the invention, a kit that facilitates the detection of fungus in a sample may comprise a first oligonucleotide that includes SEQ ID NO. 1, a second oligonucleotide that includes SEQ ID NO. 3, and an indication of a result that signifies the presence of fungus in the sample. The kit may further comprise a third oligonucleotide that includes SEQ ID NO. 2. The kit may further comprise a fourth oligonucleotide that includes SEQ ID NO. 4. The kit may further comprise a fifth oligonucleotide that includes SEQ ID NO. 5. The result may be any result, such as a Ct value. The indication may be any indication, such as a positive control or a written Ct value. If the indication comprises a written indication, it may be provided via the Internet.

The present invention provides among other things: a single-mixture RTPCR assay capable of identifying the vast majority of fungal species.

It is an object of the invention to provide unbiased fungal discovery.

It is an object of the invention to provide a tool that allows the analysis of samples without a priori knowledge of the fungi present in the sample or whether or not there is fungus present in the sample.

It is an object of the invention to improve diagnosis of fungal infections.

DESCRIPTION OF THE FIGURES

A more complete understanding of the present invention may be derived by referring to the detailed description when considered in connection with the following illustrative figures.

Figure 1:
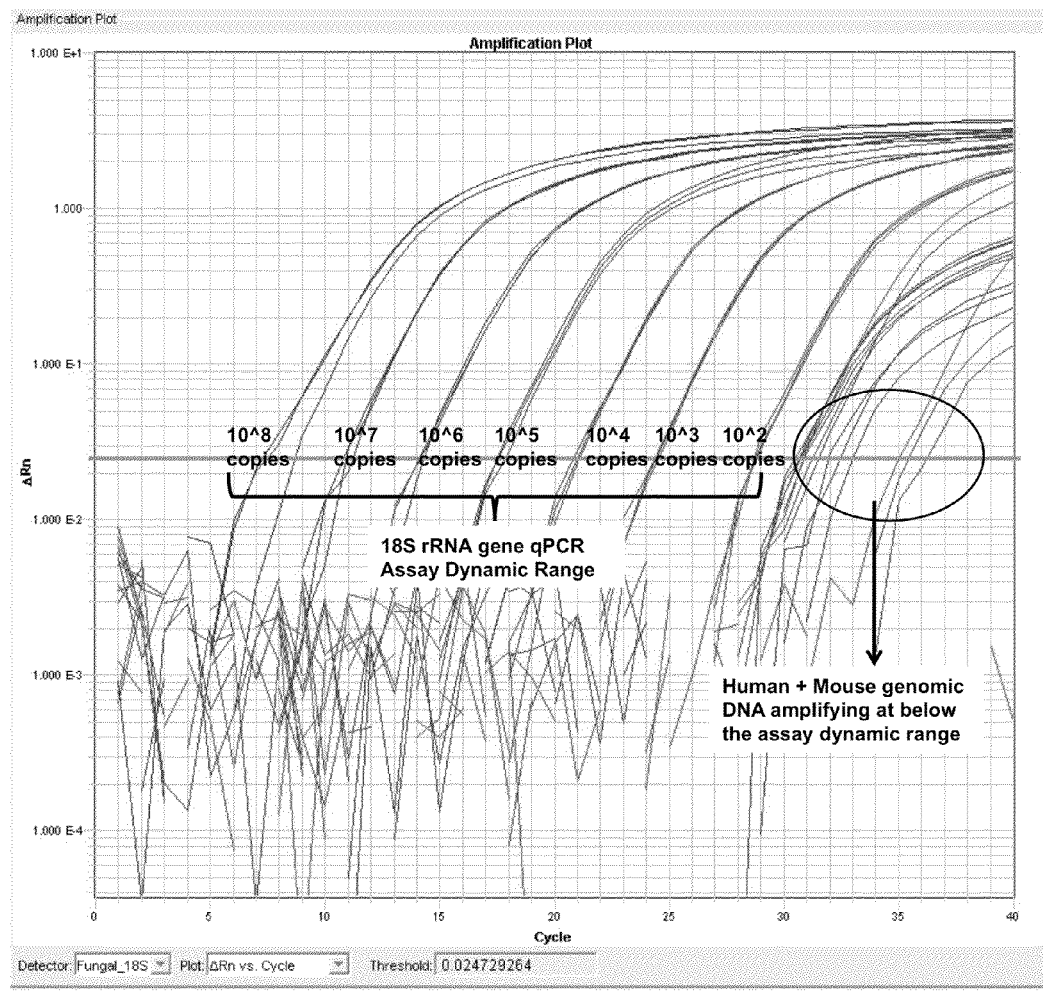
FIG. 1 depicts an amplification plot of a standard curve consisting of the indicated number of copies of 18S rRNA using SEQ ID NO. 1 and SEQ ID NO. 3 as primers and SEQ ID NO. 2 as a probe. Note that human and mouse 18S rRNA amplifies below the dynamic range of the assay

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. Aspects and applications of the invention presented here are described below in the drawings and

DETAILED DESCRIPTION OF THE INVENTION

If the provisions of 35 U.S.C. §112, ¶ 6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known presently or later-developed, equivalent structures, material or acts for performing the claimed function.

The present invention comprises a method that uses a set of oligonucleotide PCR primers that is capable of detecting well over 90% of the known species of fungi in a sample. The present invention further encompasses a method that creates a set of standards of known copy number that may be used to quantify the total fungus present in a sample. The primer set comprises a forward primer and a reverse primer. The primers are degenerate primers with multiple nucleotides that may be substituted at the indicated sites. Therefore, the primers may be provided as a mixture of primers with different nucleotides substituted at the indicated sites. Each primer of the primer mixture may be present in equal amounts or different primers in the primer mixtures may be present in unequal proportions. The invention may also encompass the use of an oligonucleotide probe capable of hybridizing to the region amplified by the forward primer and the reverse primer. Quantitative PCR platforms may use such a probe labeled with a fluorescent label and a quencher molecule in order to help quantify the amount of the specific nucleic acid present in the sample.

In some embodiments of the invention, the amplification is performed with a forward primer and a reverse primer intended to amplify the entirety of the 18S rRNA gene of a sample. This is intended to produce an amplification product that may be used as either a standard (after the copy number of the amplification product is determined) or as a library that includes the 18S rRNA from all fungal species in a sample. These primers may also comprise sequences that facilitate cloning of the amplification product into a cloning vector such as restriction enzyme sites.

In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA,) amplification with Qβ replicase, whole genome amplification with enzymes such as φ29, whole genome PCR, in vitro transcription with Klenow or any other RNA polymerase, or any other method by which copies of a desired sequence are generated.

Polymerase chain reaction (PCR) is a particular method of amplifying DNA, generally involving the making of a reaction mixture by mixing a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage (typically 80-100° C.) an annealing stage with a temperature that may based on the melting temperature (Tm) of the primers and the degeneracy of the primers, and an extension stage (for example 40-75° C.)

Quantitative PCR incorporates a detectable reporter into the reaction mixture in order to quantify the amount of template amplification. The detectable reporter may be, for example, a fluorescent label. The signal from the reporter may be detectable upon incorporation into the amplified DNA as is the case with the SYBR Green molecule. Alternatively, the detectable reporter may be linked to an oligonucleotide probe such as in the case of TaqMan™ quantitative PCR.

The oligonucleotide probe may also comprise a quencher molecule. The quencher hides from detection the majority of the fluorescence that may be emitted by the fluorescent label when the oligonucleotide probe is in solution. PCR amplification removes the quencher from the probe, rendering the fluorescent molecule detectable. Therefore the quantity or intensity of the fluorescence may be correlated with the amount of product formed in the reaction. One skilled in the art would be capable of calculating the amount of target nucleic acid (either DNA or RNA) present in a reaction mixture comprising a sample from the quantity of the change in fluorescence. Examples of fluorescent labels that may be used in quantitative PCR include but need not be limited to: HEX, TET, 6-FAM, JOE, Cy3, Cy5, ROX, TAMRA, and Texas Red. An oligonucleotide probe used in quantitative PCR may also comprise a quencher. Examples of quenchers that may be used in quantitative PCR include, but need not be limited to TAMRA (which may be used with any of a number of fluorescent labels such as HEX, TET, or 6-FAM), BHQ1, BHQ2, or DABCYL.

An oligonucleotide probe may include any label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected.

When a nucleic acid such as a primer, oligonucleotide, oligonucleotide probe or any nucleic acid sequence includes a particular sequence, the sequence may be a part of a longer nucleic acid or may be the entirety of the sequence. The nucleic acid that includes the sequence may contain nucleotides 5' of the sequence, 3' of the sequence, or both. The concept of a nucleic acid including a particular sequence further encompasses nucleic acids that contain less than the full sequence that are still capable of specifically hybridizing to the target sequence under any conditions to which a mixture comprising a nucleic acid may be subjected.

A nucleic acid may be identified by the IUPAC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60% 70%, 80%, 90%, 95%, 99% or 100% identity to the identifying sequence may still be encompassed by the invention if it is able of binding to its complimentary sequence and/or priming nucleic acid amplification of a desired target sequence. If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence.

Quantitative PCR primers with degenerate sequences may also be supplied as a primer mixture with nucleotides meeting the conditions set by the degenerate primer sequence. For example, a primer mixture including SEQ ID NO. 1 may comprise a mixture of GGAAAACTCACCAGGTCCAG (SEQ ID NO. 6), and GGGAAACTCACCAGGTCCAG (SEQ ID NO. 7). A primer mixture including SEQ ID NO. 3 may comprise a mixture of GCACTATCCCCAGCACGA (SEQ ID NO. 8), GCACTATCCCCATCACGA (SEQ ID NO. 9), GCTCTATCCCCAGCACGA (SEQ ID NO. 10), GCTCTATCCCCATCACGA (SEQ ID NO. 11), GGACTATCCCCAGCACGA (SEQ ID NO. 12), GGACTATCCCCATCACGA (SEQ ID NO. 13), GGTCTATCCCCAGCACGA (SEQ ID NO. 14). and GGTCTATCCCCATCACGA (SEQ ID NO. 15). A primer mixture including SEQ ID NO. 4 may comprise a mixture of GGAGAAAGAGCCTGAGA (SEQ ID NO. 16), GGAGAAGGAGCCTGAGA (SEQ ID NO. 17), GGAGAGAGAGCCTGAGA (SEQ ID NO. 18), and GGAGAGAGAGCCTGAGA (SEQ ID NO. 19). A primer mixture including SEQ ID NO. 5 may comprise a mixture of CTAGGAATTCCTCGTTCAAG (SEQ ID NO. 20), CTAGGAATTCCTCGTTGAAG (SEQ ID NO. 21), CTAGGCATTCCTCGTTCAAG (SEQ ID NO. 22), CTAGGCATTCCTCGTTGAAG (SEQ ID NO. 23), CTAGGGATTCCTCGTTCAAG (SEQ ID NO. 24), CTAGGGATTCCTCGTTGAAG (SEQ ID NO. 25), CTAGGTATTCCTCGTTCAAG (SEQ ID NO. 26), and CTAGGTATTCCTCGTTGAAG (SEQ ID NO. 27).

An oligonucleotide includes any DNA or RNA reagent of two or more nucleotides, whether from a natural source, artificially synthesized, or produced through the use of recombinant DNA technology. A nucleotide is an individual deoxyribonucleotide or ribonucleotide base such as A, C, G, T, or U. An oligonucleotide is often engineered to be capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

The invention encompasses methods of identifying fungi through the use of DNA sequencing, such as Sanger sequencing, next generation sequencing, pyrosequencing, SOLID sequencing, massively parallel sequencing, pooled, and barcoded DNA sequencing or any other sequencing method now known or yet to be disclosed.

In Sanger Sequencing, a single-stranded DNA template, a primer, a DNA polymerase, \nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfyrlase enayme converts pyrophosphate into ATP which in turn catalyzes the conversion of luciferin to oxyluciferin which results in the generation of visible light that is then detected by a camera.

In SOLID sequencing, the molecule to be sequenced is fragmented and used to prepare a population of clonal magnetic beads (in which each bead is conjugated to a plurality of copies of a single fragment) with an adaptor sequence and alternatively a barcode sequence The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

An oligonucleotide may be added to a mixture by any of a number of methods including manual methods, mechanical methods, or any combination thereof. An oligonucleotide may be added to a mixture by adding the mixture to an oligonucleotide that is conjugated to a substrate such as in a microarray. One may also add the oligonucleotide to a mixture in which the target allele to which the nucleic acid has specificity is absent.

In some aspects of the invention, an oligonucleotide is bound to a substrate such as a microarray. Examples of microarrays include constructs in which a plurality of single stranded oligonucleotide probes are affixed to a substrate such as silicon glass. Oligonucleotides with a sequence complementary to an allele are capable of specifically binding to that allele to the exclusion of alleles that differ from the specific allele by one or more nucleotides. Labeled sample DNA may be hybridized to the oligonucleotides and detection of the label is correlated with binding of the sample and consequently the presence of the target nucleic sample. Alternatively, PCR including quantitative PCR may be performed in an array format.

Any oligonucleotide bound to a substrate may be covalently bound to the substrate or it may be bound by some non covalent interaction including electrostatic, hydrophobic, hydrogen bonding, Van Der Waals, magnetic, or any other interaction by which the oligonucleotide may be attached to a substrate while maintaining its ability to recognize the allele to which it has specificity. A substrate may be any solid or semisolid material onto which a probe may be affixed, attached or printed, either singly or in the presence of one or more additional probes or samples. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or a PCR reaction. The sample may be bound to a substrate in the case of a Southern Blot.

The invention encompasses methods of detecting the presence of fungus in a sample. A sample may be derived from anywhere that a fungus or any part of a fungus including fungal spores, buds, or hyphae may be found including soil, air, water, solid surfaces (whether natural or artificial,) culture media, foodstuffs, and any interfaces between or combinations of these elements. A sample may be derived from a subject, such as a plant or animal, including humans. Samples derived from animals include but are not limited to biopsy necropsy, or other in vivo or ex vivo collection of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF,) cerebrospinal fluid, semen, amniotic fluid, lacrimal fluid, stool, urine, hair, or any other source of material that may be collected from a living or dead animal. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may be suspected of containing a fungus if they are derived from a subject displaying symptoms of a fungal infection or from an environmental sample from an area in which a fungus is thought to be present.

Examples of fungi that may be detected using the invention include but need not be limited to: pathogenic fungi such as *Candida quercitrusa, Absidia corymbifera, Acremonium strictum, Aspergillus flavus, Aspergillus fumigatus, Aspergillus nidulans, Aspergillus niger, Aspergillus versicolor, Aureobasidium pullulans, Candida albicans, Candida famata, Candida guilliermondii, Candida haemulonii, Candida intermedia, Candida lusitaniae, Candida pararugosa, Candida rugosa, Candida tropicalis, Chaetomium globosum, Coccidioides sp. Corynespora cassiicola, Cryptococcus neoformans, Cunnighamella bertholletiae, Epidermophyton floccosum, Exophiala dermatitidis, Fonsecaea pedrosoi, Fusarium equiseti, Fusarium oxysporum, Fusarium solani, Geotrichum candidum, Geotrichum capitatum, Malassezia furfur, Microsporum canis, Microsporum gypseum, Neurospora crassa, Paecilomyces lilacinus, Paecilomyces sinensis, Paecilomyces variotii, Penicillium marneffei, Pichia ohmeri, Rhizopus microsporus, Rhizopus oryzae, Rhodotorula minuta, Rhodotorula mucilaginosa, Rhodotorula slooffiae, Saccharomycopsis crataegensis, Scedosporium apiospermum, Scedosporium prolificans, Sporothrix schenckii, Stephanoascus ciferrii, Trichophyton mentagrophytes, Tri-* chophyton rubrum, Trichosporon asahii, Trichosporon asteroides, Trichosporon cutaneum, Trichosporon dermatis, Trichosporon faecale, Trichosporon montevideense, Trichosporon mucoides, and Trichosporon ovoides as well as environmental fungi such as Gigaspora gigantea, Acaulospora "brown", Hebeloma crustuliniformae, Comprinus micaceous, Sarcosphaera crassa, Pholiota destruens, Pleurotus ostreatus, Cortinarius sp., Helvella queletii, Sclerogaster xerophila, Melanogaster magnisporas, Sedecula pulvinata, Elaphomyces decipiens, Clavulina cristata, Rizopogon sp, Hebeloma crustuliniformae, Tricholoma polulinum, Lactarius sp., Cortinarius sp., Agaricus sp., Xanthomendoza galericulata, Endoconidioma sp., Cladosporium cladosporioides, Phoma sp., Cytospora sp., and Alternaria sp.

The invention further encompasses kits containing components that facilitate the performance of any of the methods encompassed by the invention. A kit may be any assemblage or collection of components that facilitates a method. A kit that facilitates the invention may include specific nucleic acids such as oligonucleotides, labeling reagents, enzymes including DNA polymerases such as Taq or Pfu, reverse transcriptase, or any other enzymes and/or reagents that facilitate detection of the target nucleic acids. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication of a result that indicates a particular outcome. For example, an indication may be a DNA sequence signifies the identification of a particular fungal phylum, class, order, family, genus species, subspecies, strain or any other delineation of a group of fungi. An indication may be a standard curve configured to quantify the amount of fungus present in a sample. An indication may include a set of standards that is included in the kit that has been premeasured with regard to copy number. An indication may be a positive control included with the kit or a set of primers and/or other reagents that may be used to generate the positive control. In the case of a quantitative PCR reaction, the indication may be a particular Ct level or a range of Ct levels. An indication may also include but need not be limited to: a level of fluorescence or radioactive decay, a value derived from a standard curve or from a control, or any combination of these and other outputs. The indication may be printed on a writing that may be included in the kit or it may be posted on the Internet or embedded in a software package.

Elements and acts in the example are intended to illustrate the invention for the sake of simplicity and have not necessarily been rendered according to any particular sequence or embodiment. The example is also intended to establish possession of the invention by the Inventors.

EXAMPLES

Example 1

Detection and Quantitation of Fungi by RT-PCR Using Pan-Fungal Primers and Probes The primers of this invention were designed to enable broad-coverage assays for the detection of fungal organisms. Sequence were exported from the Silva ribosomal RNA database (available at the World Wide Web: arb-silva.de) and used to generate massive multiple sequence alignment files for the 18S rRNA gene, the 5.8 rRNA gene, and the 28S rRNA gene from all major fungi phyla. The sequence filter setting in the primer design software was optimized in order to capture the maximal number of sequences. A base distribution file was generated from the multiple sequence alignment files by summarizing the number of sequences with each base (A, T, C, G) at each locus. Regions with at least 6 bases at >99% conservation at the 3' end of the primer (5'-3' direction) were then identified using a combination of Tm assessment and degeneracy minimization (n=3 or less).

After the primer/probe design, specificity of the primer set was checked by BLAST searching against all human, bacteria, and mouse nucleotide sequences in GenBank using all permutations possible with the resultant primer sets. Primers with no cross reactivity to human, bacteria, and mouse sequences were selected. A set of degenerate PCR primers and a pan-fungal probe targeting the 18S rRNA gene was generated and tested on a variety of fungal isolates by qPCR (see FIGS. 1-6.). The forward primer of the primer set includes SEQ ID NO. 1 and the reverse primer includes SEQ ID NO. 3. Either the forward primer or the reverse primer may be less than 100 nucleotides, less than 75 nucleotides, less than 50 nucleotides, or less than 30 nucleotides in length. The probe includes SEQ ID NO. 2 and may also be less than 100 nucleotides, less than 75 nucleotides, less than 50 nucleotides or less than 30 nucleotides in length.

| SEQ ID | Name | Sequence |
|---|---|---|
| SEQ ID NO. 1 | PanFungal_18S_F | 5'-GGRAAACTCACCAGG TCCAG-3' |
| SEQ ID NO. 2 | PanFungal_18S_prb | 5'-TGGTGGTGCATGGCC GTT-3' |
| SEQ ID NO. 3 | PanFungal_18S_R | 5'-GSWCTATCCCCAKCA CGA-3' |

Processing of samples for the isolation of fungal DNA for performance of quantitative PCR is as follows: Liquid specimens are thawed on ice, vortexed for 5-10 seconds, and centrifuged at 8000 rpm for 30 seconds using airtight bucket swing rotors. This collects sample droplets at the bottom of the tube. 50 µl of RLT buffer (from the Qiagen AllPrep DNA/RNA/Protein Kit) are aliquotted into pre-labelled microtubes. 100 µl of sample are then transferred into the prelabelled microtube, keeping air bubbles to a minimum. Samples are lysed in a Barocycler (Pressure Biosciences Inc.) The microtubes are removed and inspected for any ruptures or collapsing. The lysate (approximately 150 µl) are then added to 550 µl of RLT buffer in an Eppendorf tube. This mixture is then centrifuged for 3 minutes at full speed in an aerosol resistant rotor in a tabletop microcentrifuge at full power. The supernatant is then transferred to an AllPrep DNA spin column (Qiagen), placed into a pre-labelled collection tube, and centrifuged for 30 seconds at 10,000 RPM. Then 500 µl of AW1 buffer (Qiagen) is added to the DNA spin column. This is centrifuged for 15 seconds at 10,000 rpm. The flow-through is discarded. 500 µl of AW2 is then added to the spin column. This assemblage is centrifuged for 2 minutes at full speed. The flow-through is discarded. The spin column is then placed in a prelabelled 2 ml elution tube. 100 µl of EB is then added to the spin column membrane. This is incubated at room temperature for 2 minutes, centrifuged for 1 minute at 10,000 rpm, and DNA is eluted. The eluted DNA is stored at −80° C. when not in use.

The pan-fungal quantitative PCR assay is performed using a master mix comprising the following concentrations: 1× Invitrogen qPCR SuperMix (Invitrogen), 40 μM of the Pan 18S_qPCR forward primer (SEQ ID NO. 1), 40 μM of the Pan 18S qPCR_reverse primer (SEQ ID NO. 3), and 20 μM of the Pan 18S qPCR probe (SEQ ID NO. 2). 0.1 μl per reaction of Hi-Di Formamide (Applied Biosystems) is added as well as sufficient ultra-pure water to bring the volume of the master mix to 10 μl per reaction. The master mix is then added in 10 μl aliquots to the reaction plate (such as a 384 well plate) and 1 μl of DNA isolated from sample or other DNA template is then added to each well.

A standard curve may be generated by creating a working stock of a known amount of plasmid standard and diluting that working stock into a standard curve by serial dilutions. For example, a $10^9$ copy per μl working stock may be diluted into $10^8$, $10^7$, $10^6$, etc. copies per μl and diluted sufficiently to result in that same number of copies per reaction.

A quantity of 20 ng of non-specific human or mouse genomic DNA may be added to inhibit binding of the primers to non-specific targets. The addition of this non-specific DNA may result in non specific amplification at Ct values less than 33.

The PCR was run on an Applied Biosystems 7900HT Fast Real-Time PCR system. Using this instrument, the conditions were as follows: 3 minutes at 50° C. for UNG treatment, 5 minutes at 95° C. for Taq Activation, then 40 cycles of 15 seconds at 95° C. and 1 minute at 65° C. The results of the quantitative PCR assay described above are depicted in FIGS. 1-6.

FIG. 1 depicts an amplification plot of a standard curve consisting of the indicated number of copies of 18S rRNA using SEQ ID NO. 1 and SEQ ID NO. 3 as primers and SEQ ID NO. 2 as a probe. The target DNA is cloned 18S rRNA. Note that human and mouse 18S rRNA amplifies below the dynamic range of the assay.

Figure 2:
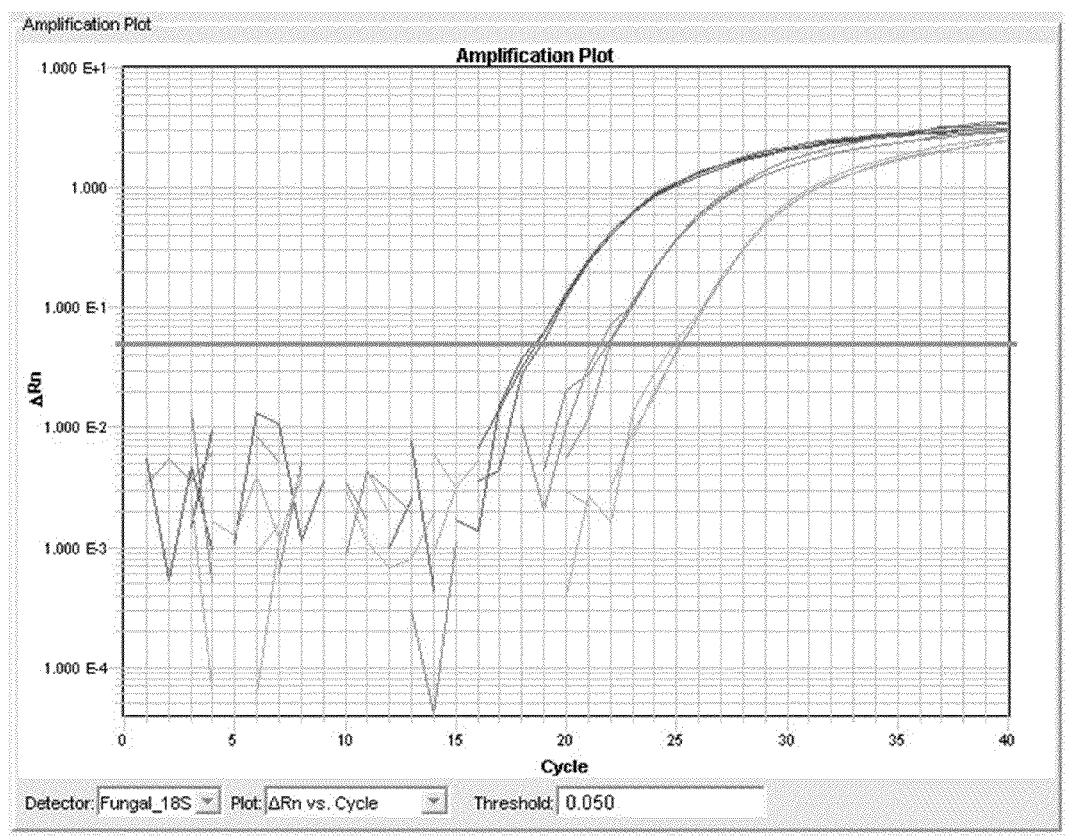
FIG. 2 depicts an amplification plot of three serial 1/10 dilutions of a sample of *Candida lusitaniae* in an assay using SEQ ID NO. 1 and SEQ ID NO. 3 as primers and SEQ ID NO. 2 as a probe.

FIG. 2 depicts an amplification plot of three serial 1/10 dilutions of a sample of *Candida lusitaniae.*

Figure 3:
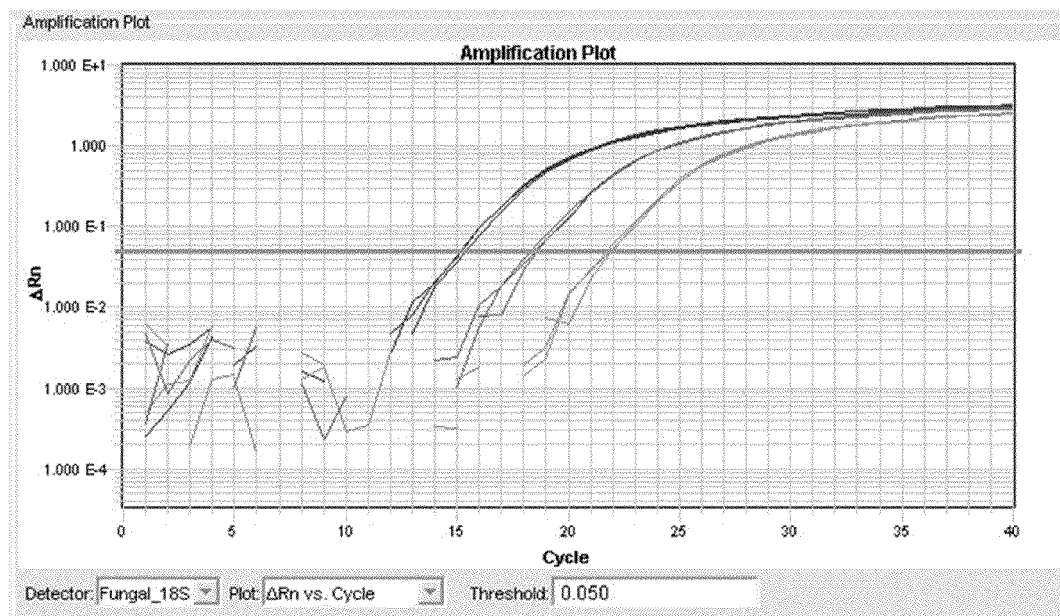
FIG. 3 depicts an amplification plot of three serial 1/10 dilutions of a sample of *Candida quercitrusa* using SEQ ID NO. 1 and SEQ ID NO. 3 as primers and SEQ ID NO. 2 as a probe.

FIG. 3 depicts an amplification plot of three serial 1/10 dilutions of a sample of *Candida quercitrusa.*

Figure 4:
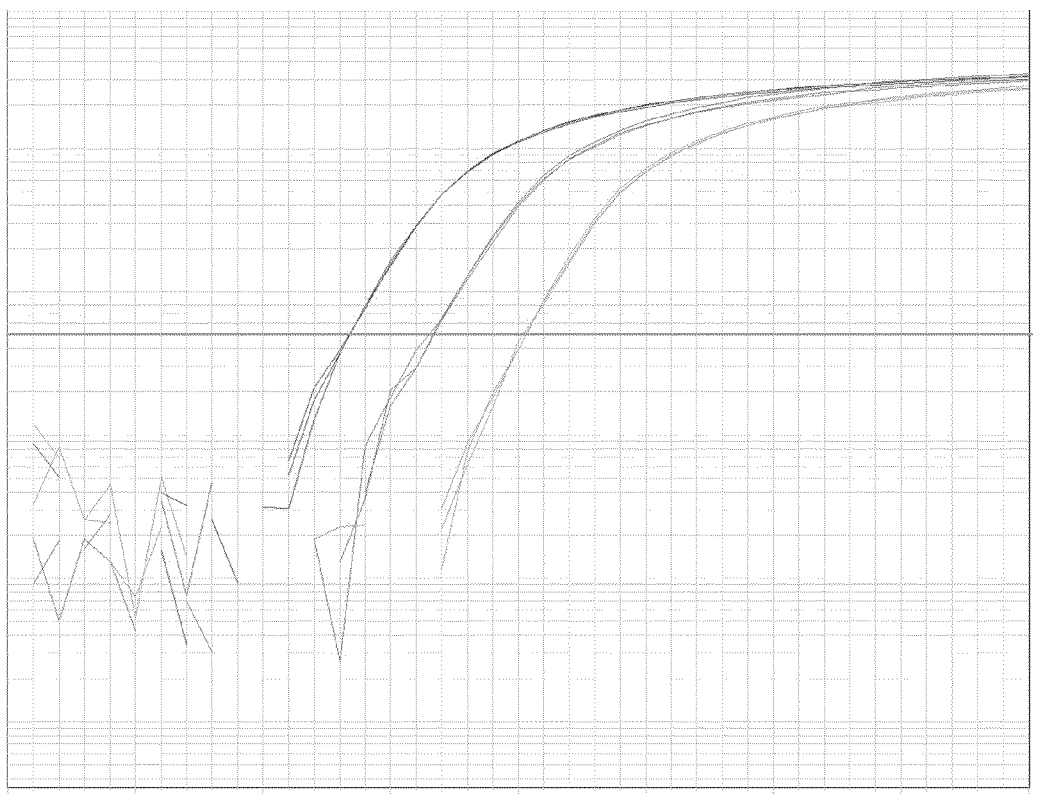
FIG. 4 depicts an amplification plot of three serial 1/10 dilutions of a sample of *Candida tropicalis* using SEQ ID NO. 1 and SEQ ID NO. 3 as primers and SEQ ID NO. 2 as a probe.

FIG. 4 depicts an amplification plot of three serial 1/10 dilutions of a sample of *Candida tropicalis.*

Figure 5:
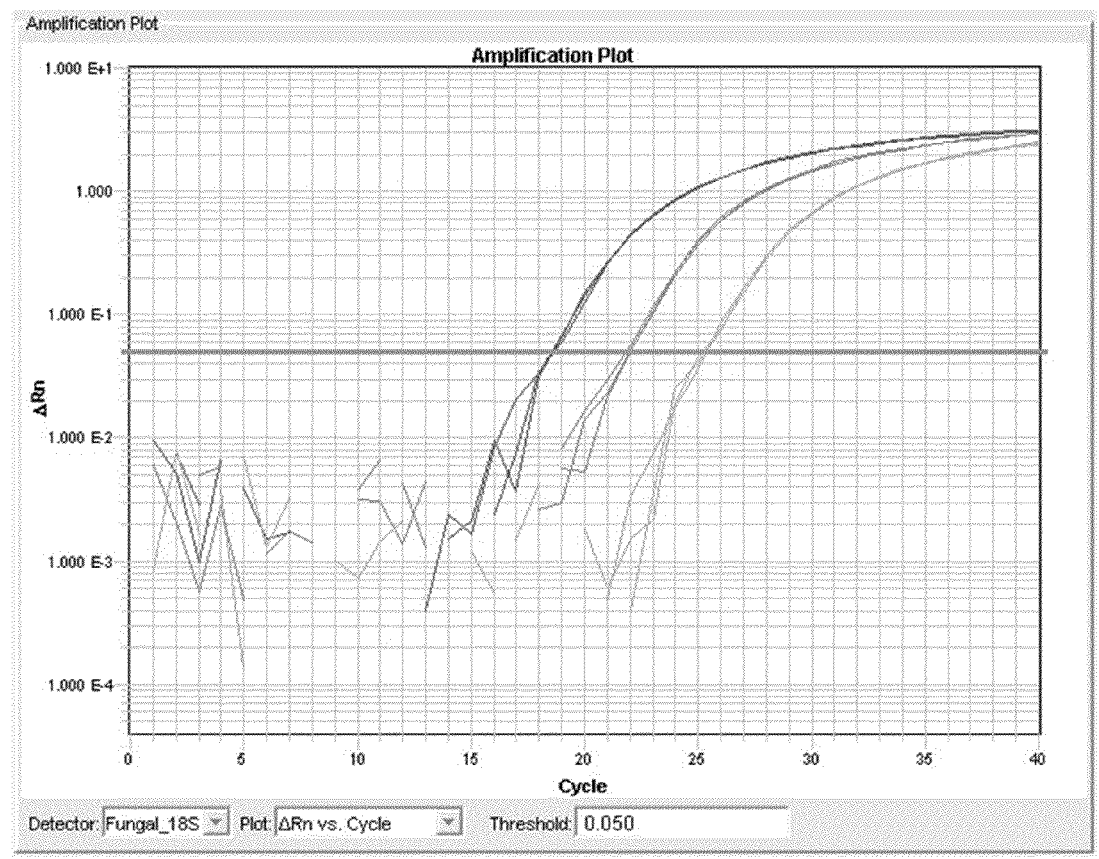
FIG. 5 depicts an amplification plot of three serial 1/10 dilutions of a sample of *Epidermophyton floccosum* using SEQ ID NO. 1 and SEQ ID NO. 3 as primers and SEQ ID NO. 2 as a probe.

FIG. 5 depicts an amplification plot of three serial 1/10 dilutions of a sample of *Epidermophyton floccosum.*

Figure 6:
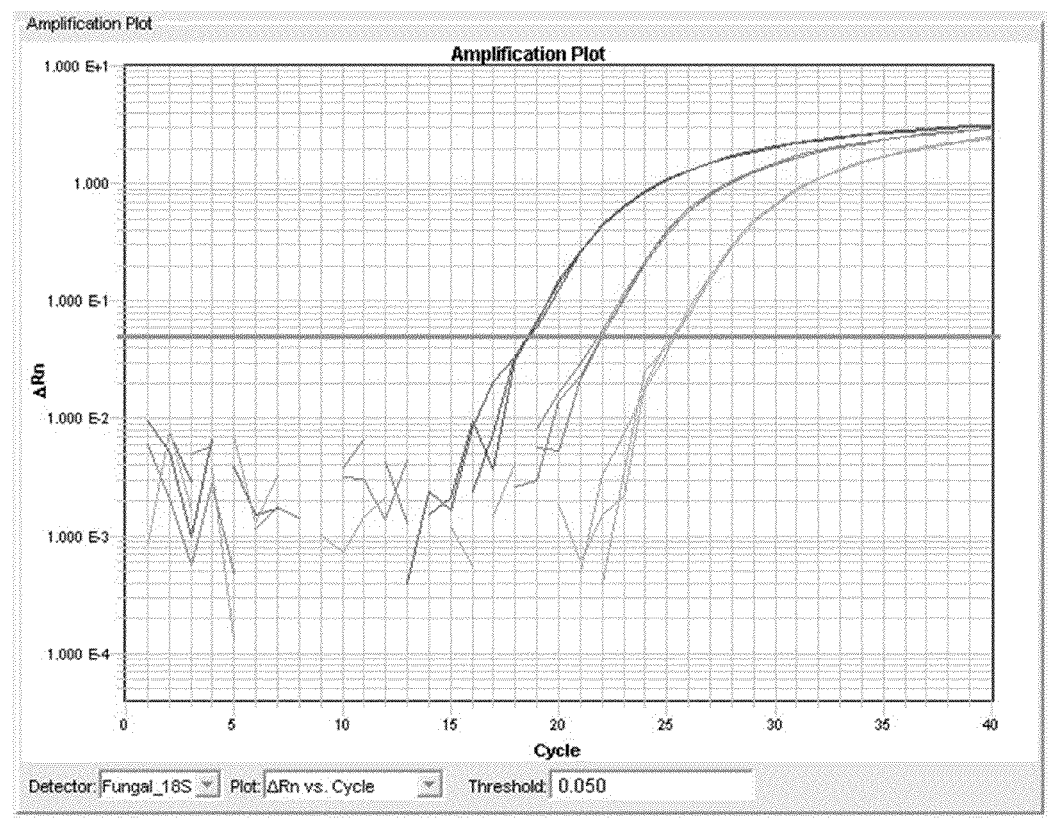
FIG. 6 depicts an amplification plot of three serial 1/10 dilutions of a sample of *Exophiala dermatiditis* using SEQ ID NO. 1 and SEQ ID NO. 3 as primers and SEQ ID NO. 2 as a probe.

FIG. 6 depicts an amplification plot of three serial 1/10 dilutions of a sample of *Exophiala dermatiditis.*

The example shows that the primers of the invention may be used in a quantitative PCR assay that detects a wide variety of fungal species.

Example 2

Ability of 18S rRNA Quantitative PCR Assay to Detect Fungal Species Relative to Other Pan-Fungal Assays In silico analysis showed that a qPCR assay using the primer/probe set represented by SEQ ID NO. 1, SEQ ID NO. 2, and SEQ ID NO. 3 has a coverage of 90.80% of all 2082 available fungal 18S rRNA gene sequences.

In silico validation of pan-fungal primers comprises two parts: a primer analysis portion and an assay analysis portion. The primer analysis code parses the primer sequence (accommodating for degeneracies). The primer location in the alignment is determined and the alignment is scanned for sequences that have poor data in that region. Once poor quality sequences are removed, the primer and its reverse complement are compared for perfect matches to each sequence in the alignment. Matched sequences and missed sequences are recorded in separate output files and the data is summarized on-screen prior to termination of the program.

The assay analysis portion scans the output files from multiple primer analysis files to determine the degree of overlap between various primers and compares them to the members of the alignment. Again, there are separate output files for misses and matches for the whole assay and an additional file that lists the identities of the primer components that matched each member of the alignment. The on-screen output is a tally of organisms that matched all assay candidates with respect to the total number of organisms in the alignment.

Use of this method to validate primers and probes in the 18S rRNA fungal detection assay (SEQ ID NO. 1, SEQ ID NO. 2, and SEQ ID NO. 3) revealed that the forward primer (SEQ ID NO. 1) was capable of recognizing 2011 out of 2082 fungal species (96.6%) in the Silva Database that had sequence data in the region that includes the hybridization site of the forward primer. The reverse primer (SEQ ID NO. 3) matched 1991 out of 2076 fungal species (95.9%) in the Silva database that had sequence data in the region that includes the hybridization site of the reverse primer. The oligonucleotide probe (SEQ ID NO. 2) was capable of recognizing 2017 our of 2082 fungal species (96.9%) in the Silva database that had sequence data in the region that includes the hybridization site of the oligonucleotide probe.

Other pan-fungal assays are unlikely to match this level of performance. For example, the forward primer from a published pan-fungal quantitative PCR assay (Einsele et al, J. Clin. Microbiol, 35 1353-1360, 1997) matched only 1779 out of 2078 (85.6%) of the fungal species in the Silva Database that had sequence data in the region that includes the hybridization site of the forward primer. The reverse primer in the same reference matched only 1617 out of 2081 (77.7%) of the fungal species in the Silva Database (available at the World Wide Web arb-silva.de/) that had sequence data in the region that includes the hybridization site of the forward primer. The probe in the same reference matched only 1387 out of 2086 fungal species (66.5%) accessed in the Silva Database.

This represents a considerable improvement over another broad-coverage fungal qPCR assay Imhof et al, *Eur J Clin Microbiol Infect Dis* 22, 558-560 (2003), which has a coverage of 68.07% of the 2082 available fungal 18S rRNA gene sequences.

Example 3

Primers Used to Generate a Cloned Standard for use in Quantitative Validation

A set of primers was generated that is capable of producing quantitative cloned standards. Clone libraries may also be generated from pan-fungal PCR primers capable of amplifying the entire 18S rRNA gene.

| SEQ ID | Name | Sequence |
|---|---|---|
| SEQ ID NO. 4 | 18S_TGEN_library_F1 | 5'-GGAGARRGAGCCTGAGA-3' |
| SEQ ID NO. 5 | 18S_TGEN_library_R1 | 5'-CTAGGNATTCCTCGTTSAAG-3' |

The SEQ ID NO. 4 and SEQ ID NO. 5 primer set was used to generate a cloned plasmid to be used in quantitative and sensitivity/specificity preliminary validation. Using the cloned standard, the assay has shown a dynamic range of $10^9$ copies/ul to $10^2$ copies/ul without amplifying human genomic DNA in this dynamic range.

Example 4

Sequencing Primers for Use in Identifying Fungal Species

Sequencing primers capable of broad coverage are necessary to assess fungal communities and unknown isolates in that they will enable fungal identification and characterization without a priori knowledge of the contents of the community or isolates. Using 18S rRNA and 23/28S rRNA sequences from the Silva database, a base distribution of the 18S rRNA and 23/28S rRNA gene sequences was established. Primers were designed to hybridize to (3') end of 18S rRNA gene and the (5') end of the 23/28S rRNA gene. This primer set facilitates nucleic acid amplification across the ITS1/5.8S/ITS2 complex, generating a 500-2000 bp amplicon that may be sequenced by any sequencing method.

| SEQ ID | Name | Sequence |
|---|---|---|
| SEQ ID NO. 28 | ITS_TGEN_F1 | 5'-CTTSAACGAGGAATNCCTAGTA-3' |
| SEQ ID NO. 29 | ITS_TGEN_R1 | 5'-CATWCCCAAACWACYCGACTC-3' |
| SEQ ID NO. 30 | ITS_TGEN_R3 | 5'-TACTTGTKYGCTATCGGTCTC-3' |

Such primers may be combined with adapters and/or barcoding sequences. In silico analysis showed that the sequencing primers SEQ ID NO. 28 and SEQ ID NO. 29 or alternatively, SEQ ID NO. 28 and SEQ ID NO. 30 were able to amplify and characterize a high percentage of the fungal species tested. The ITS_TGEN_F1 forward primer (SEQ ID NO. 28) matched 1941 out of 2057 (94.36%) fungal species in the 18S rRNA gene and the ITS_TGEN_R1 reverse primer (SEQ ID NO. 29) matched 996 out of 1101 (90.46%) sequences in the 23S/28S rRNA gene. The primer set referenced in Imhof et al, *Eur J Clin Microbiol Infect Dis* 22, 558-560 (2003) failed to reach this level. The references ITS1-R (CAGGAGACTTRTAYACGGTCCAG, SEQ ID NO. 31) matched only 60 out of 1093 (5.49%) sequences, ITS 1-F (CTTGGTCATTTAGAGGAAGTAA, SEQ ID NO. 32) matched 743 of the 1626 (45.69%) sequences and ITS 1-F_ext (WTGGTYDYNNAGAGGAAGTAA, SEQ ID NO. 33) matched 775 of the 1627 (47.63%) sequences.

All materials cited herein are hereby incorporated by reference in their entirety.

We claim:

1. A method of detecting a fungus in a sample, the method comprising the steps of:
   adding a first forward primer that includes SEQ ID NO. 1 to a first mixture, wherein the first mixture comprises a nucleic acid isolated from the sample;
   adding a first reverse primer that includes SEQ ID NO. 3 to the first mixture; and
   adding a second forward primer that includes SEQ ID NO. 4 to a second mixture comprising a nucleic acid isolated from the sample;
   adding a second reverse primer that includes SEQ ID NO. 5 to the second mixture;
   subjecting the first and the second mixture to conditions that allow nucleic acid amplification; and
   detecting the presence of the fungus based on a result of nucleic acid amplification in both the first and the second mixture.

2. The method of claim 1, wherein the second forward primer comprises a second forward primer mixture and wherein the second forward primer mixture comprises SEQ ID NO. 16, SEQ ID NO. 17, SEQ ID NO. 18, and SEQ ID NO. 19.

3. The method of claim 1, wherein the second reverse primer comprises a second reverse primer mixture and wherein the second reverse primer mixture comprises SEQ ID NO. 20, SEQ ID NO. 21, SEQ ID NO. 22, SEQ ID NO. 23, SEQ ID NO. 24, SEQ ID NO. 25, SEQ ID NO. 26, and SEQ ID NO. 27.

4. The method of claim 1, wherein the second forward primer and the second reverse primer each comprises a cloning sequence that facilitates cloning the product of the nucleic acid amplification into a nucleic acid vector.

5. The method of claim 4, wherein the cloning sequence comprises a restriction endonuclease site.

6. The method of claim 4, further comprising ligating the product into the nucleic acid vector.

7. The method of claim 6, further comprising measuring the copy number of the nucleic acid vector.

8. The method of claim 7, further comprising diluting the nucleic acid vector to generate a standard set.

9. The method of claim 8, further comprising comparing a result of the nucleic acid amplification of the first mixture to a result of a nucleic acid amplification of a third mixture, wherein the third mixture comprises a standard from the standard set and further comprising quantifying the amount of fungus in the sample.

10. A method of generating a clone library from a sample, the method comprising:

adding a forward primer that includes SEQ ID NO. 4 to a mixture comprising a nucleic acid isolated from the sample;

adding a reverse primer that includes SEQ ID NO. 5 to the mixture; and subjecting the mixture to nucleic acid amplification.

11. The method of claim 10, wherein the forward primer and the reverse primer each comprises a sequence that facilitates cloning into a nucleic acid vector.

12. The method of claim 11, further comprising isolating a product of the nucleic acid amplification and ligating the product into the nucleic acid vector.

13. The method of claim 12, wherein the nucleic acid vector comprises a plasmid vector.

14. The method of claim 1, further comprising the step of adding an oligonucleotide probe to the first mixture, wherein said oligonucleotide probe contains less than full sequence of SEQ ID NO.2 and hybridizes to the amplified sequence.

15. The method of claim 14, wherein said probe has at least 80% sequence homology with SEQ ID NO. 2.

16. The method of claim 1, wherein the first forward primer comprises fewer than 50 nucleotides.

17. The method of claim 1, wherein the first reverse primer comprises fewer than 50 nucleotides.

18. The method of claim 1, further comprising adding an oligonucleotide probe to the first mixture; wherein the oligonucleotide probe includes SEQ ID NO. 2.

19. The method of claim 18, wherein the oligonucleotide probe comprises fewer than 50 nucleotides.

20. The method of claim 18, wherein the oligonucleotide probe comprises a fluorescent label.

21. The method of claim 20, wherein the fluorescent label is selected from the group consisting of HEX, TET, 5-FAM, 6-FAM, JOE, Cy3, Cy5, ROX, TAMRA, dR110, dR6G, VIC, NED, dROX PET, Gold540, LIZ, and Texas Red.

22. The method of claim 18, wherein the oligonucleotide probe comprises a quencher.

23. The method of claim 22, wherein the quencher is selected from the group consisting of TAMRA, BHQ1, BHQ2, BHQ+, or DABCYL.

24. The method of claim 1, wherein the first forward primer comprises a first forward primer mixture comprising forward primers that include SEQ ID NO. 6 and SEQ ID NO. 7.

25. The method of claim 24, wherein 50% of the forward primers in the first forward primer mixture include SEQ ID NO. 6.

26. The method of claim 1, wherein the first reverse primer comprises a first reverse primer mixture comprising reverse primers that include SEQ ID NO. 8, SEQ ID NO. 9, SEQ ID NO. 10, SEQ ID NO. 11, SEQ ID NO. 12, SEQ ID NO. 13, SEQ ID NO. 14, and SEQ ID NO. 15.

27. The method of claim 1, wherein the sample is from a subject.

28. The method of claim 27, wherein the subject is an animal.

29. The method of claim 27, wherein the subject is a human.

30. The method of claim 1, wherein the sample is from an environmental source.

31. The method of claim 1, wherein the result comprises a Ct value.

32. A method of detecting a fungus in a sample, the method comprising:

adding a forward primer that includes SEQ ID NO. 4 to a mixture, wherein the mixture comprises a nucleic acid isolated from the sample;

adding a reverse primer that includes SEQ ID NO. 5 to the mixture;

subjecting the mixture comprising the forward and reverse primers to conditions that allow nucleic acid amplification; and detecting the presence of the fungus based on a result of nucleic acid amplification in the mixture.

33. The method of claim 32, wherein the forward primer comprises a forward primer mixture comprising SEQ ID NO. 16, SEQ ID NO. 17, SEQ ID NO. 18, and SEQ ID NO. 19.

34. The method of claim 32, wherein the reverse primer comprises a reverse primer mixture comprising SEQ ID NO. 20, SEQ ID NO. 21, SEQ ID NO. 22, SEQ ID NO. 23, SEQ ID NO. 24, SEQ ID NO. 25, SEQ ID NO. 26, and SEQ ID NO. 27.

35. The method of claim 32, wherein the forward primer and the reverse primer each comprises a cloning sequence that facilitates cloning the product of the nucleic acid amplification into a nucleic acid vector.

36. The method of claim 35, wherein the cloning sequence comprises a restriction endonuclease site.

37. The method of claim 35, further comprising ligating the product into the nucleic acid vector.

38. The method of claim 37, further comprising measuring copy number of the nucleic acid vector.

39. The method of claim 38, further comprising diluting the nucleic acid vector to generate a standard set.

40. The method of claim 39, further comprising comparing a result of the nucleic acid amplification of the first mixture to a result of a nucleic acid amplification of a third mixture, wherein the third mixture comprises a standard from the standard set and further comprising quantifying the amount of fungus in the sample.

41. The method of claim 32, wherein the sample is from a subject.

42. The method of claim 41, wherein the subject is an animal.

43. The method of claim 42, wherein the subject is a human.

44. The method of claim 32, wherein the sample is from an environmental source.

45. The method of claim 32, wherein the result comprises a Ct value.

* * * * *

SEQUENCE LISTING

<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer/probe

<400> SEQUENCE: 1
ggraaactca ccaggtccag                                           20

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide probe

<400> SEQUENCE: 2
tggtggtgca tggccgtt                                             18

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 3
gswctatccc cakcacga                                             18

<210> SEQ ID NO 4
<211> LENGTH: 17

```
<212> TYPE: DNA
<213> ORGANISM: Artificial Sequence
<220> FEATURE:
<223> OTHER INFORMATION: Oligonucleotide primer

<400> SEQUENCE: 4
ggagarrgag cctgaga                                                      17

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (6)..(6)
<223> OTHER INFORMATION: n is a, c, g, or t

<400> SEQUENCE: 5
ctaggnattc ctcgttsaag                                                   20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
ggaaaactca ccaggtccag                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
gggaaactca ccaggtccag                                                   20

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 8
gcactatccc cagcacga                                                     18

<210> SEQ ID NO 9
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 9
gcactatccc catcacga                                                     18

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide primer
```

```
<400> SEQUENCE: 10
gctctatccc cagcacga                                                18

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 11
gctctatccc catcacga                                                18

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 12
ggactatccc cagcacga                                                18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 13
ggactatccc catcacga                                                18

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 14
ggtctatccc cagcacga                                                18

<210> SEQ ID NO 15
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 15
ggtctatccc catcacga                                                18

<210> SEQ ID NO 16
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 16
ggagaaagag cctgaga                                                 17

<210> SEQ ID NO 17
<211> LENGTH: 17
```

```
<212> TYPE: DNA
<213> ORGANISM: Artificial Sequence
<220> FEATURE:
<223> OTHER INFORMATION: Oligonucleotide primer

<400> SEQUENCE: 17
ggagaaggag cctgaga                                                    17

<210> SEQ ID NO 18
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 18
ggagagagag cctgaga                                                    17

<210> SEQ ID NO 19
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 19
ggagagagag cctgaga                                                    17

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
ctaggaattc ctcgttcaag                                                 20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 21
ctaggaattc ctcgttgaag                                                 20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 22
ctaggcattc ctcgttcaag                                                 20

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
ctaggcattc ctcgttgaag                                                 20
```

```
<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 24
ctagggattc ctcgttcaag                                              20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
ctagggattc ctcgttgaag                                              20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
ctaggtattc ctcgttcaag                                              20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 27
ctaggtattc ctcgttgaag                                              20

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (15)..(15)
<223> OTHER INFORMATION: n is a, c, g, or t

<400> SEQUENCE: 28
cttsaacgag gaatncctag ta                                           22

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 29
catwcccaaa cwacycgact c                                            21

<210> SEQ ID NO 30
<211> LENGTH: 21
```

```
<212> TYPE: DNA
<213> ORGANISM: Artificial Sequence
<220> FEATURE:
<223> OTHER INFORMATION: Oligonucleotide primer

<400> SEQUENCE: 30
tacttgtkyg ctatcggtct c                                              21

<210> SEQ ID NO 31
<211> LENGTH: 23
<212> TYPE: DNA
<213> ORGANISM: Artificial Sequence
<220> FEATURE:
<223> OTHER INFORMATION: Oligonucleotide primer/probe

<400> SEQUENCE: 31
caggagactt rtayacggtc cag                                            23

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide primer/probe

<400> SEQUENCE: 32
cttggtcatt tagaggaagt aa                                             22

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide primer/probe
<220> FEATURE:
<221> NAME/KEY: misc_feature
<222> LOCATION: (9)..(10)
<223> OTHER INFORMATION: n is a, c, g, or t

<400> SEQUENCE: 33
wtggtydynn agaggaagta a                                              21
```